United States Patent [19]

O'Brien et al.

[11] Patent Number: 4,462,963

[45] Date of Patent: Jul. 31, 1984

[54] ANALYTICAL FURNACE

[75] Inventors: Larry S. O'Brien, St. Joseph; Ward S. Kaler, Benton Harbor, both of Mich.

[73] Assignee: Leco Corporation, St. Joseph, Mich.

[21] Appl. No.: 355,213

[22] Filed: Mar. 5, 1982

[51] Int. Cl.³ .................. G01N 25/02; G01N 31/12
[52] U.S. Cl. ........................... 422/78; 373/130; 414/153; 422/63; 422/80
[58] Field of Search ................. 422/63, 78, 80; 414/153; 373/110, 115, 118, 128, 130, 133

[56] References Cited

U.S. PATENT DOCUMENTS 1,495,503  5/1924  Armstrong ...................... 373/128
2,332,943  10/1943  Sobers .............................. 422/78
2,966,537  12/1960  Witucki et al. ................. 373/134
3,092,681  6/1963  Malm ................................ 373/130

Primary Examiner—Michael S. Marcus
Attorney, Agent, or Firm—Price, Heneveld, Huizenga & Cooper

[57] ABSTRACT

The specification discloses an analyzer having a furnace defining a furnace chamber and including a floor with an aperture communicating with the chamber. A sample-supporting platform is provided and movable between an analyzing position within said furnace chamber and a loading position below the level of, and out from under, the furnace. A plurality of heating elements extend into the furnace chamber and are insulatively sealed therein by a pair of slotted members which cooperate to reduce airflow along the elements.

1 Claim, 10 Drawing Figures

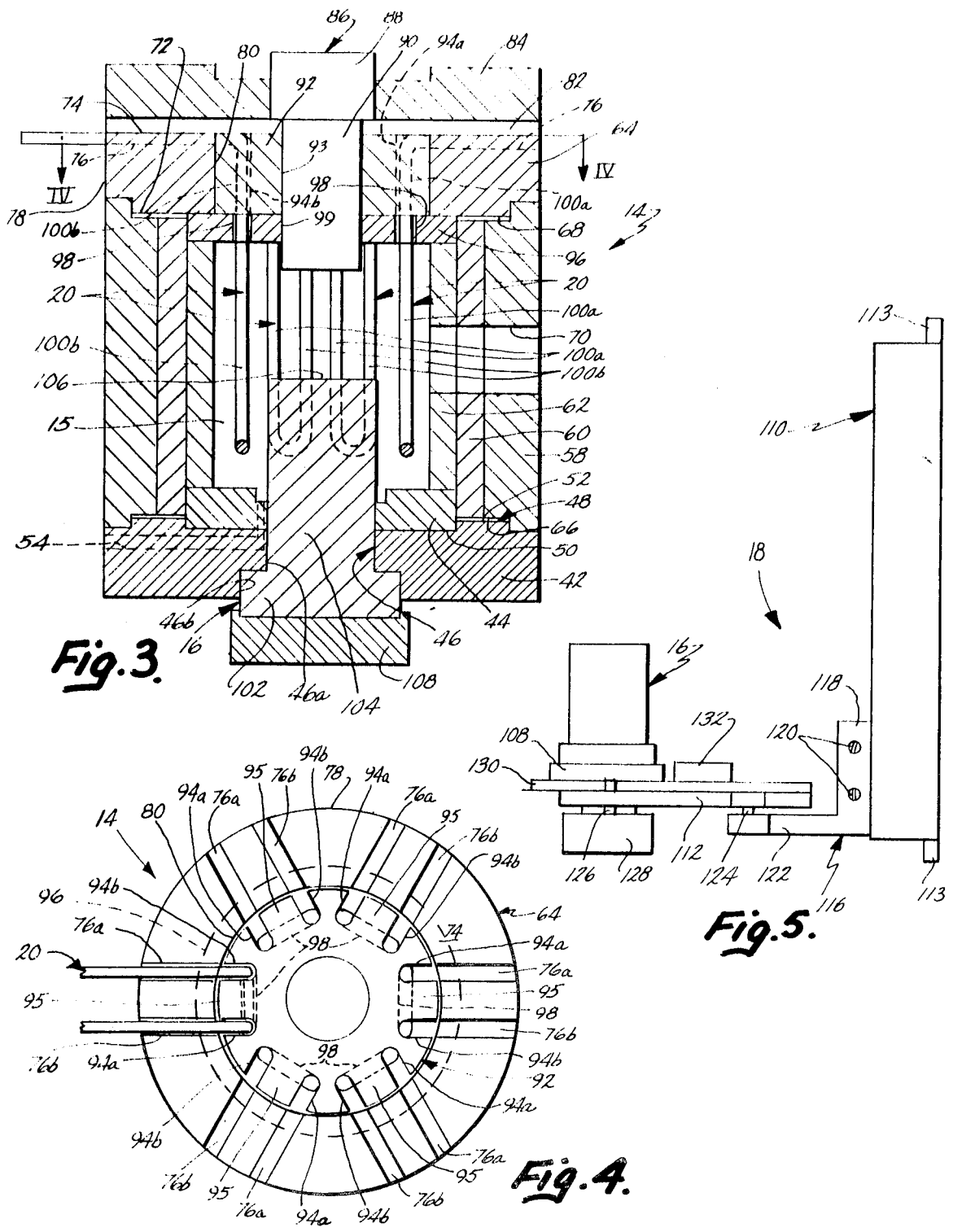

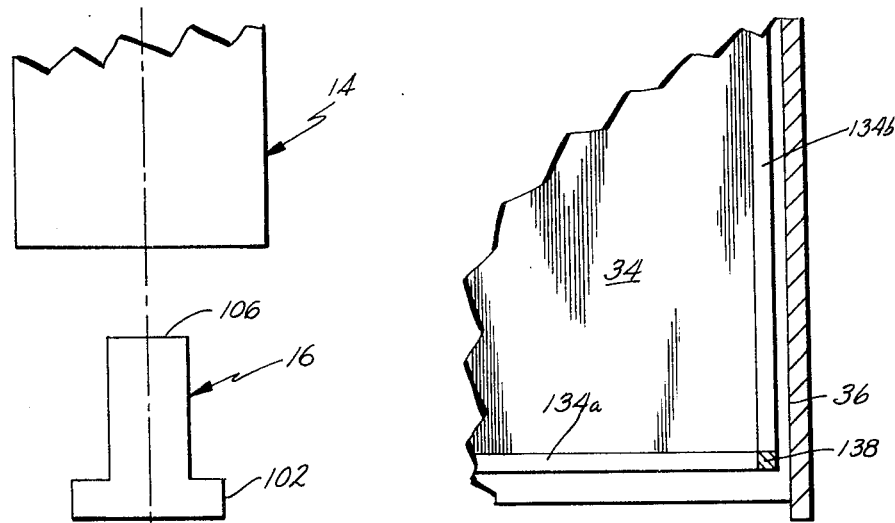
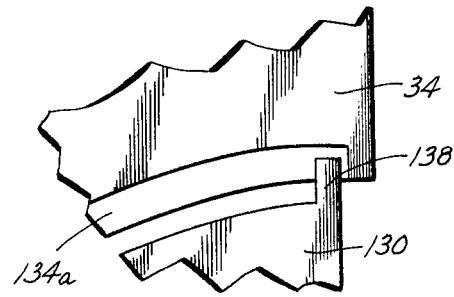
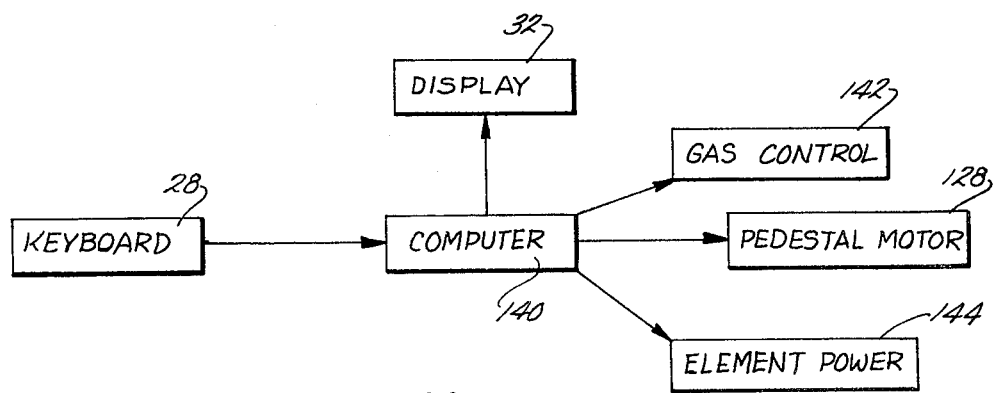

ANALYTICAL FURNACE

BACKGROUND OF THE INVENTION

The present invention relates to analytical apparatus, and more particularly to analytical furnaces.

A wide variety of analytical furnaces have been developed to test material samples under controlled temperature and environmental conditions. Such furnaces are used, for example, to perform ash fusion tests by inserting the ash samples into the furnace; ramping the temperature within the furnace chamber; and observing the samples to determine the various deformation temperatures of the ash.

One known analyzer includes a generally cylindrical furnace, defining a furnace chamber and including a floor having an aperture communicating with the chamber. The analyzer further includes a sample-supporting platform generally concentrically aligned with the furnace floor aperture and vertically shiftable between an analyzing position, wherein the platform is located within the furnace, and a loading position, wherein the platform is located below the furnace. The platform is relatively difficult to load and unload because the platform, even in the loading position is located directly under the furnace. Consequently, samples may be placed on and removed from the platform only by reaching underneath the furnace and more particularly between the lowered platform and the furnace floor. The typical location of the furnace and sample platform in a rear portion of the analyzer further complicate sample handling.

Analytical furnaces of the resistance type include a plurality of electric heating elements extending through the furnace wall and into the furnace chamber. Usually, the furnace includes a removable cover, and the heating elements extend between the upper surface of the furnace side wall and the cover. However, the apertures, channels, or bores required to accommodate the heating elements permit air within chamber to exit the furnace relatively rapidly. This makes furnace temperature regulation difficult and increases the furnace power requirements, and cost of operating the analyzer. Although gaskets have been positioned between the heating elements and various portions of the furnace in an attempt to seal the heating elements within the furnace, these gaskets are relatively fragile and easily broken. Further, the gaskets are typically ring-shaped members which may be positioned in only one fixed position between the upper surface of the furnace wall and the furnace cover.

SUMMARY OF THE INVENTION

The aforementioned problems are solved by the present invention. According to one aspect of the present invention, an analyzer furnace is provided which includes a furnace chamber, and a sample-supporting platform movable between an analyzing position, wherein the platform is supported within the furnace chamber, and a loading position, wherein the platform is located remote from the furnace for convenient access.

According to another aspect of the present invention, a plurality of heating elements extend through the furnace and into the furnace chamber with first and second insulating members, defining first and second slot means, respectively, cooperatively receiving various portions of the heating elements such construction greatly reduces heat loss through the furnace wall at the points where the elements extend therethrough. In a preferred embodiment, the first and second slot means are angularly oriented with respect to one another. Because the slots are angularly oriented with respect to one another, a portion of the first member restricts airflow through exposed portions of the second slot means, and similarly portions of the second member restrict airflow through the exposed portions of the first slot means. With the heat loss of the furnace reduced, the temperature within the chamber can be more precisely regulated, and the power requirements of the furnace are reduced.

These and other objects, advantages, and features of the invention will be more fully understood and appreciated by reference to the written specification and appended drawings.

BRIEF DESCRIPTION OF THE DRAWINGS

FIG. 3 is a vertical cross-sectional view of the furnace;

FIG. 4 is a cross-sectional view of the furnace taken along plane IV—IV in FIG. 3;

FIG. 5 is a side elevational view of the lifting and pivoting mechanism supporting the sample pedestal;

FIG. 7 is a fragmentary, side elevational view of the sample pedestal shown in its inoperative position;

FIG. 8 is a fragmentary, cross-sectional view taken along line VIII—VIII in FIG. 2;

FIG. 9 is a fragmentary, top plan view of the structure shown in FIG. 8; and

FIG. 10 is a block electrical circuit diagram showing the control circuit for the furnace.

DESCRIPTION OF THE PREFERRED EMBODIMENT

Figure 2:
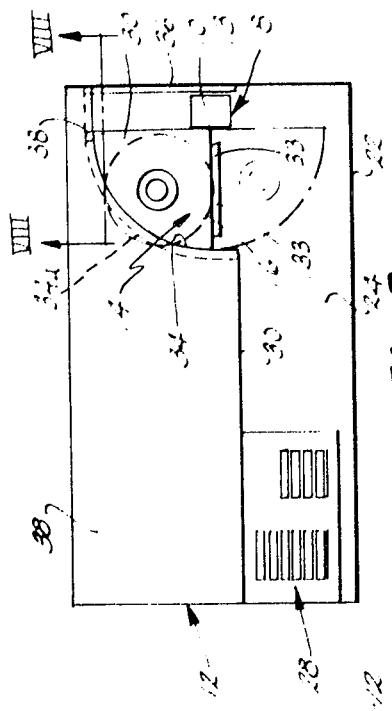
FIG. 2 is a top plan view, partially broken away, of the analyzer with the furnace shown in phantom.
Figure 6:
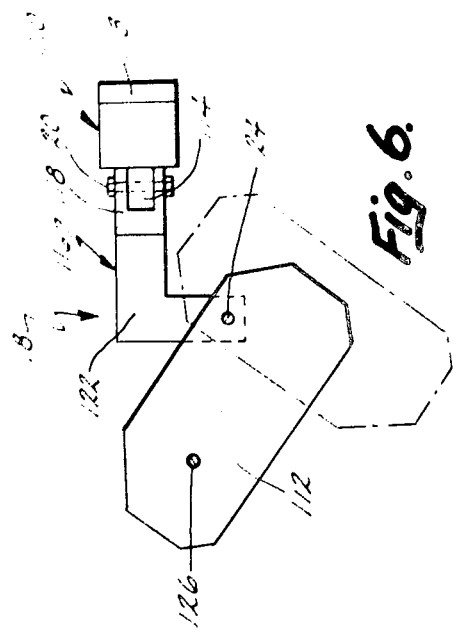
FIG. 6 is a top plan view of the mechanism shown in FIG. 5 with the sample pedestal, sensor, and work platform removed and showing two positions of the support platform.
Figure 1:
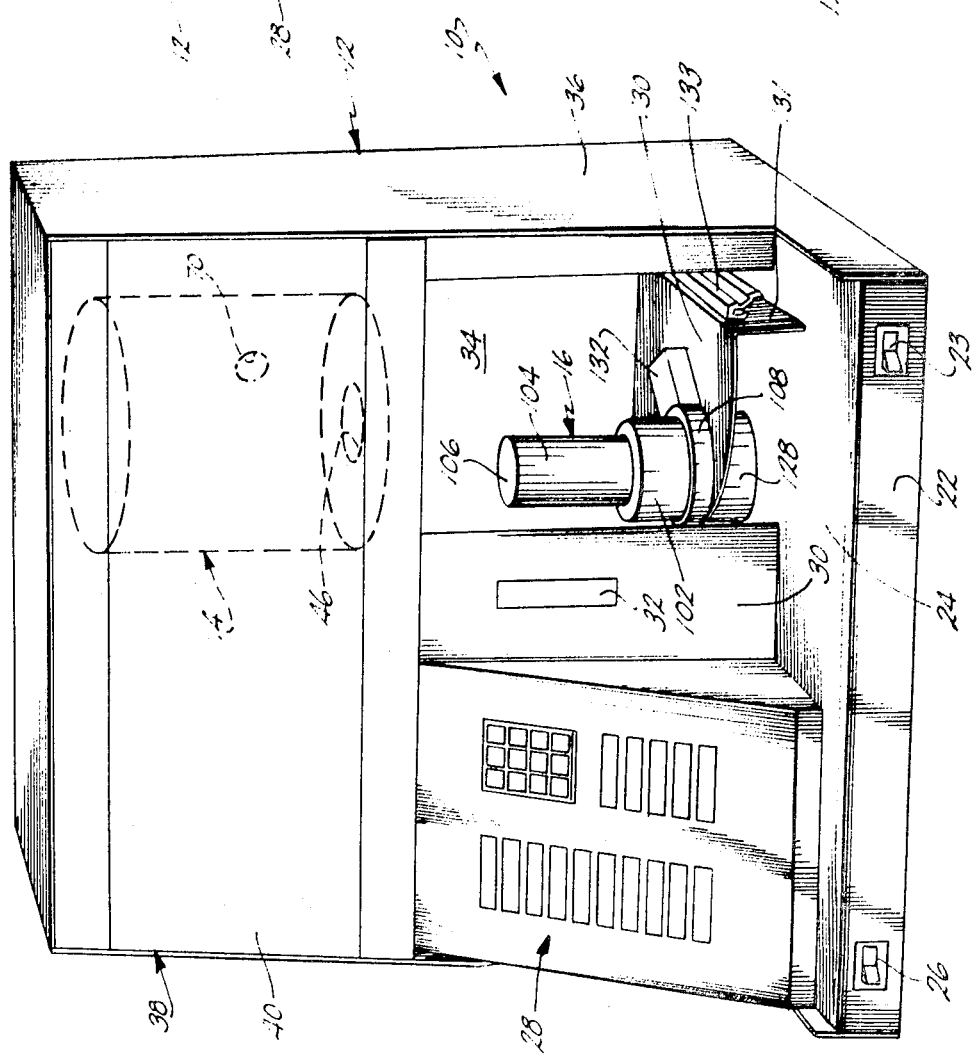
FIG. 1 is a perspective view of an analyzer furnace incorporating the present invention shown in a sample-loading/unloading position.

An analyzer furnace constructed in accordance with a preferred embodiment of the invention is illustrated in the drawings and generally designated 10. As seen in FIGS. 1 and 2, analyzer 10 includes a housing, or cabinet, 12, a furnace 14 supported within the housing and defining a furnace chamber 15 (FIG. 3). The analyzer furnace also includes a sample pedestal 16, and pedestal transportation mechanism 18 (FIGS. 2, 5, and 6). A plurality of heating elements 20 (FIG. 3) are positioned within furnace chamber and controlled to supply heat for the fusion of a sample.

Housing 12 (FIGS. 1 and 2) includes a generally rectangular base 22 defining a generally horizontal work area 24. A main power switch 26 (FIG. 1) is positioned within base 22 to provide main power control for the furnace. A keyboard 28 (FIGS. 1 and 2) is mounted on base 22 and inclined rearwardly and upwardly therefrom and a display panel 30 extends perpendicularly upwardly from base 22 adjacent to the keyboard and includes a display 32. An arcuate pedestal compartment wall 34 extends from display panel 30 to a side 36 of housing 12. As seen in FIG. 2, wall 34 has an arcuate cross section of one-quarter segment of a circle. A furnace cabinet 38 is supported above keyboard 28, display panel 30, and compartment wall 34 and includes a smoked-glass front window 40. Cabinet 38 is generally rectilinear and supports furnace 14 in a manner well known to those having ordinary skill in the art.

Furnace 14 (FIGS. 1 and 3) has a generally cylindrical outer sidewall 58 with a circular floor 42 and hearth 44 together comprising the lower portion of the furnace. Both floor 42 and hearth 44 are generally annular members which together define a stepped bore 46 having narow portion 46a and wide portion 46b. Upper surface 48 of floor 42 defines a generally circular depression, or pocket, 50 in which hearth 44 is positioned. The diameter of pocket 50 is generally identical to the outside diameter of hearth 44 so that floor 42 and hearth 44 closely interfit with one another. Additionally, floor 42 defines an annular ridge 52 which centers the furnace side walls on floor 42 as will be described. A tubular bore 54 extends radially through floor member 42 generally perpendicularly to axial bore 46 and then upwardly through both floor 42 and hearth 44 to communicate with furnace chamber 15. A carrier or reaction gas may be introduced into chamber 15 by attaching a pressurized gas source to bore 54.

The furnace side wall includes outer liner 58, middle liner 60, inner liner 62, and element support 64. All of concentrically positioned liners 58, 60, and 62 are generally cylindrical and dimensioned to closely interfit with one another. The inside diameter of inner liner 62 defines the lateral extent of chamber 15 and has an outer diameter substantially the same as both the inner diameter of middle liner 60 and the outer diameter of hearth 44. Likewise, middle liner 60 has an outer diameter substantially the same as the inner diameter of outer liner 58. Outer line 58 additionally defines lower and upper annular depressions 66 and 68, respectively, which center outer liner with respect to the other components of furnace 14. Outer liner 58 is positioned on floor member 42 with ridge 52 extending into and closely interfitting with depression 66 to center floor 42 with respect to the outer liner. Middle liner 60 closely interfits with hearth 44 and rests on ridge 52. Finally, inner liner 62 rests on hearth 44. A generally cylindrical, radially extending bore 70 serves as a viewing port and extends through liners 58, 60, and 62 and provides a means for observing samples within furnace chamber 15, particularly during heating.

At the top of the furnace sidewall is a generally annular support member 64 having an outer diameter generally identical to the outer diameters of outer liner 58 and floor 42. Support 64 includes a downwardly extending annular ridge 72 having an outside diameter substantially identical to the diameter of pocket 68. Support 64 (see also FIG. 4) rests on outer liner 58 with ridge 72 positioned within pocket 68 to center the support with respect to the outer liner. The inner diameter of support 64 is generally identical to the inner diameter of inner liner 62. The upper surface 74 of element support 64 is generally planar and includes six spaced pairs of element receiving channels 76a and 76b. Each pair of channels 76a and 76b are oriented generally parallel to one another and extend from outer surface 78 to inner surface 80 of member 64. Additionally, each pair of channels 76a and 76b extend generally parallel to a radius of support 64 extending between the channels.

A gasket 82 is positioned on top of, and has an outside diameter generally identical to, element support 64.

Similarly, a cover 84 rests on, and has an outside diameter generally identical to, gasket 82. A top plug 86 is a generally cylindrical member having an enlarged upper cylindrical portion 88 integrally joined to a reduced diameter, lower cylindrical portion 90. The outside diameter of lower portion 90 is generally identical to the inner diameter of gasket 82, and the outside diameter of enlarged portion 88 is generally identical to the inner diameter of cover 84. Consequently, plug 86 closely interfits with cover 84 and gasket 82 and rests on the gasket.

The furnace also includes an element spacer 92 (FIGS. 3 and 4) which is a generally cylindrical member having an outside diameter generally identical to the inside diameter of support 64 and an axially extending bore 93 with a diameter generally identical to the outer diameter of lower portion 90 of plug 86. Spacer 92 includes six slot pairs 94 each including slots 94a and 94b which extend generally vertically through the spacer and which extend inwardly from the outer surface of the member. Each of pairs 94a and 94b are elongated in a generally radial direction with respect to spacer 92 and located to align with channels 76a and 76b, respectively, in support 64. Additionally, each slot pair 94a and 94b is generally parallel to one another and to a radius of spacer 92 extending therebetween. A lobe 95 is defined by each slot pair 94a and 94b.

A generally annular furnace chamber cover 96 has an outer diameter generally identical to the inner diameter of middle liner 60 and center bore 99 with a diameter generally identical to the outside diameter of lower portion 90 of plug 86. Ceiling or cover 96 rests on the top annular surface of inner liner 62 and in turn supports spacer 92 positioned directly above. Cover 96 is a generally planar member and includes six generally evenly spaced elongated slots 98 (FIG. 3) extending therethrough. Each of the slots 98 is located below a pair of slots 94a and 94b in spacer 92 so that an elongated U-shaped heating element may be inserted downwardly through elongated slot pairs 94a and 94b and through a vertically aligned slot 98. Slots 94 and 98 have their longitudinal axis oriented in angular relationship with respect to one another and, in the preferred embodiment, are generally perpendicular. As can be seen in FIG. 3, each of lobes 95 of spacer 92 substantially covers the center portion of an associated slot 98 between the legs 100 of a heating element 20.

A plurality of heating elements 20 (FIGS. 3 and 4) extend downwardly into chamber 15. Elements 20 are commercially available and preferably are fabricated of molybdenum disilicide. Each of elements 20 is a generally U-shaped member including a pair of parallel legs 100a and 100b which extend horizontally through channels 76a and 76b, respectively, in support member 64 downwardly through the slots 94a and 94b in spacer 92, through slots 98 in the ceiling 96 and into furnace chamber 15. Elements 20 are powered in a manner well known through an electrical power source 144 (FIG. 10) to generate heat within chamber 15. As seen in FIG. 4, channels 76 and slots 94 and 98 are dimensioned to closely receive legs 100 of element 20. Thus, the outside diameter of legs 100a and 100b are substantially the same as the width of channels 76 and slots 94. Further, the outer spacing between legs 100a and 100b is substantially the same as tangentially extending slots 98 formed through cover 96. Members 92 and 96 thereby cooperate to seal elements 20 within furnace 14 restricting air from flowing upwardly along element legs 100a and 100b. As can be appreciated, each of the members forming furnace 14 and member 16 are made of a suitable refractory ceramic material such as alumina.

The sample-supporting pedestal 16 (FIGS. 1 and 3) includes a generally cylindrical base portion 102 and a narrower cylindrical platform portion 104 integrally joined thereto and extending upwardly therefrom. A generally horizontally extending sample platform 106 comprises the upper surface of pedestal 16. Pedestal 16 is supported within an aluminum cup 108, which is a generally cup-shaped, annular member.

Pedestal transportation mechanism 18 (FIGS. 5 and 6) generally includes rodless cylinder 110 and support plate 112 pivotally coupled thereto. Cylinder 110 is commercially available from Origa Corporation of Elmhurst, Illinois as Type 200/20. Cylinder 110 is secured to the side 36 of housing 12 (see FIG. 2) by securing brackets 113 to the housing side using screws. Cylinder 110 integrally includes a vertically shiftable element 114 which travels upwardly and downwardly along the height of the cylinder. An L-shaped bracket 116 has a bifurcated leg 118 secured to shiftable element 114 using bolts 120. The generally horizontal leg 122 of bracket 116 extends from leg 118. Support 112 is a generally planar member pivotally supported in a generally horizontal orientation on leg 122 by a pivot pin 124. Consequently, platform 112 is free to pivot in a generally horizontal plane about the generally vertical axis of pin 124. A work platform 130 (FIGS. 1, 2, and 5) is secured in overlying relationship to member 112 using screws. Platform 130 includes an integral front 131 supporting a handle 133 for manually pivoting member 112 and members 130 and 16 supported thereby. A drive shaft 126 is rotatably supported within platform 112 through member 130 and may be driven by an electric motor 128 fixedly mounted on the underside of member 112. A cup 108 is supported on the end of drive shaft 126 for rotation therewith. Consequently, if motor 128 is actuated, drive shaft 126 rotates cup 108 and pedestal 16. This rotational action insures uniform heating and minimal temperature gradients throughout the sample. A sensor 132 is mounted on work platform 130 adjacent cup 108 for detecting its rotational position. The construction and operation of sensor 132 is more fully described in copending application Ser. No. 355,171, entitled ASH FUSION SYSTEM, filed on even data herewith, assigned to the assignee of the present application, the disclosure of which is incorporated herein by reference.

FIGS. 2, 8, and 9 illustrate the guiding mechanism for restricting movement of work platform 130 and consequently sample platform 106 to a predetermined horizontal plane and a predetermined vertical line. Compartment wall 34 includes a groove means 134 including a horizontal groove 134a and a generally vertical groove 134b proximate side 36 and communicating with groove 134a. A stud, or projection, 138 extends from work platform 130 into groove 134. Stud 138 may move only within groove 134, which together serve as an interlock limiting movement of the work platform 130 and sample platform 106 supported thereon to movement only along a predetermined horizontal plane or only along a predetermined vertical line. When projection 138 is positioned within groove 134b, pedestal 16 is concentrically aligned with bore 46 and furnace 14 so that when pedestal 16 is shifted upwardly it will travel into furnace 14 as seen in FIG. 3. As stud 138 travels within groove 134, pedestal 16 may be shifted to and between three basic positions. The analyzing position is illustrated in FIG. 3 wherein pedestal 16 is vertically, or concentrically, aligned with bore 46 and fully inserted into chamber 14. When so positioned, sample platform 106 is located in a central portion of chamber 15 generally aligned with port 70. As stud 138 travels downwardly within groove 134b, by the actuation of cylinder 110 pedestal 16 is extracted from furnace 14 to an inoperative position indicated in FIGS. 2 and 7 wherein the pedestal is generally vertically aligned with the furnace; however, with sample platform 106 located below the furnace and in alignment therewith. As stud 138 travels within groove 134a and away from groove 134b, pedestal 16 is pivoted horizontally to its loading position shown in FIG. 1 and in phantom in FIG. 2 wherein sample platform 106 is located below furnace 14 and out from under the furnace. Thus, if cylindrical furnace 14 were extended downwardly, the imaginary extension would not pass through any portion of pedestal 16 in the loading position.

FIG. 10 illustrates the control system of the analyzer which employs a computer 140 including suitable interface circuits. The computer is coupled to a keyboard 28, to receive command signals therefrom, and has an output port coupled to a display 32, pedestal motor 128, gas control 142, and element power source 144, to send suitable control signals thereto. Computer 140 is programmed in a conventional manner to control the furnace as described herein. Gas control 142 is any well-known device such as a solenoid valve for introducing gases into bore 54 (see FIG. 3), and element power source delivers electric current to heating elements 20 (see FIG. 3).

Operation

When analyzer furnace 10 is to be operated, the desired information regarding temperature and environment to be maintained within furnace chamber 15 during an analysis is entered through keyboard 28 into computer 140. Pedestal 16 is moved to its loading position, as indicated in FIG. 1 and in phantom in FIG. 2, wherein platform 106 is positioned below and out from under furnace 14 by grasping platform handle 133 and pivoting the platform forwardly. The samples to be analyzed are then placed on platform 106 and optionally may be placed in a sample tray which is in turn placed on platform 106. The operator then grasps handle 133 and pivots work platform 130 about pivot pin 124 so that pedestal 16 is horizontally shifted to its operative position indicated in FIGS. 2 and 7 with platform 106 vertically aligned with furnace 14 and located below the furnace. As member 130 is so pivoted, stud 138 travels within horizontal groove 134a to the position indicated in FIG. 8. The operator presses the cylinder up/down switch 23 causing the cylinder to shift element 114 upwardly, carrying work platform 130 and pedestal 16 upwardly into the analysis position shown indicated in FIG. 3. Stud 138 insures that pedestal 16 may not be shifted upwardly until the pedestal has been pivoted back into its operative position with stud 138 located as indicated in FIG. 8. Likewise, once pedestal 16 begins traveling upwardly so that stud 138 enters groove 134b, work platform 130 and pedestal 116 cannot be pivoted forwardly toward the loading position.

After pedestal 16 has been fully raised into the analyzing position, computer 140 issues appropriate signals to gas control 142, pedestal motor 128, and elemental power 144 to produce the desired temperature, environment, and pedestal rotation as selected by the operator.

Computer 140 may change these control signals during the analysis to change the temperature or the environment within chamber 15 without extracting pedestal 16. The condition of samples on platform 106 may be observed through viewport 70 through glass 40 during sample analysis as described in the above-identified co-pending application to monitor the condition of the samples.

When analysis is complete as determined by computer 140, signals are issued to gas control 142 and elemental power 144 to terminate the introduction of gas into chamber 15 and to cut power to heating elements 20, respectively. After a cooling period, the operator activates the up/down switch 23 to control cylinder 110 which causes element 114 to travel downwardly along cylinder 110 conveying pedestal 16 to the lower, or inoperative, position as indicated in FIGS. 2 and 7. The operator may then grasp handle 133 and rotate work platform 130 so that pedestal 16 shifts horizontally to the loading position as indicated in FIG. 1 and in phantom in FIG. 2. The samples on platform 106 are then visually inspected and removed for subsequent processing.

Heating elements 20 are insulatably sealed within furnace 14 in part by cooperating spacer 92 and ceiling 96. Members 92 and 96 cooperate to reduce airflow along elements 20 and out of furnace 14. Slots 94 and 98 are angularly oriented with respect to one another so that the portions of slots 98 between legs 100a and 100b are covered by one of lobes 95 on member 92. Additionally, spacer 92 facilitates proper spacing of the elements 20 within chamber 15 evenly about the chamber.

If an element 20 must be replaced for any reason, plug 86, roof 84, and gasket 82 are first removed from the furnace 14. The element 20 to be replaced is then disconnected from power source 144 and spacer 92 is withdrawn from supporter 64 by pulling the spacer directly upwardly extracting the spacer from the furnace. The element 20 to be replaced is then pulled directly upwardly out of member 96 with the element passing out of its associated slot 98. A new element is then inserted through the empty slot 98 and seated within the associated channels 76a and 76b in support 64. Spacer 92 is then reinserted aligning slots 94 with spacers 20, and more particularly with legs 100. Gasket 82 is then replaced to seal elements 20 within supporter 64. Cover 84 and plug 86 are also replaced.

It should be understood that the above description is intended to be that of a preferred embodiment of the invention. Various changes and alterations might be made without departing from the spirit and broader aspects of the invention as set forth in the appended claims, which are to be interpreted in accordance with the principles of patent law, including the doctrine of equivalents.

The embodiments of the invention in which an exclusive property or privilege is claimed are defined as follows:

1. An analytical furnace comprising:
   a housing;
   a furnace enclosure supported by said housing and defining a furnace chamber, said furnace enclosure including a lower portion having an aperture communicating with said chamber;
   platform means supported by said housing for supporting samples to be analyzed;
   means for moving said platform between a raised, analyzing position, wherein said platform extends through said aperture and is located within said furnace chamber, and a lowered position in which said platform and any samples supported thereon are located below said furnace enclosure;
   means for permitting movement of said platform between said lowered position and a remote loading position, wherein said platform is located out of vertical alignment with said furnace chamber to facilitate loading and unloading of samples on said platform;
   means for restricting horizontal movement of said platform between said loading and lowered positions and for restricting vertical movement of said platform between said lowered and analyzing positions, said restricting means, comprising means defining a groove in said housing, said restricting means further comprising a follower extending from said platform means into said groove whereby said follower can move only within said groove;
   a generally U-shaped heating element extending downwardly through said furnace enclosure into said furnace chamber and including a pair of elongated spaced legs joined at one end;
   said furnace enclosure including a first insulating member defining a first elongated slot through which said spaced legs extend into said chamber; and
   said furnace enclosure further including a second insulating member overlying said first insulating member and defining second and third elongated slots through which said spaced legs extend, neither of said second or third elongated slot being linearly aligned with said first elongated slot to reduce air flow through said insulating members along and about said spaced legs.

* * * * *